United States Patent [19]

Diamond et al.

[11] 3,959,488

[45] May 25, 1976

[54] 1-SUBSTITUTED BIGUANIDES FOR TREATING HYPERACIDITY OR ULCERATION

[75] Inventors: Julius Diamond, Lafayette Hill; George H. Douglas, Paoli; Bernard J. Burns, Philadelphia, all of Pa.

[73] Assignee: William H. Rorer, Inc., Fort Washington, Pa.

[22] Filed: Dec. 6, 1973

[21] Appl. No.: 422,454

Related U.S. Application Data

[60] Division of Ser. No. 189,195, Oct. 14, 1971, Pat. No. 3,800,043, which is a continuation-in-part of Ser. No. 89,005, Nov. 12, 1970, abandoned.

[52] U.S. Cl. ............................................. 424/326
[51] Int. Cl.² ........................................... A01N 9/20
[58] Field of Search ................................... 424/326

[56] References Cited

FOREIGN PATENTS OR APPLICATIONS 649,692   1/1951   United Kingdom ................ 424/326

OTHER PUBLICATIONS

Brit. J. Pharmacol. (1948), 3, 346–349; 3, 350–351; 3, 352–353.

Primary Examiner—Frederick E. Waddell
Attorney, Agent, or Firm—James A. Nicholson

[57] ABSTRACT

The 1-substituted biguanides of this invention possess useful gastric anti-secretory and spasmolytic properties. Compounds of this type which also display anti-hypertensive and CNS depressant properties are also disclosed.

6 Claims, No Drawings

1-SUBSTITUTED BIGUANIDES FOR TREATING HYPERACIDITY OR ULCERATION

CROSS REFERENCE TO RELATED APPLICATIONS

This is a Divisional Application of U.S. Ser. No. 189,195 filed Oct. 14, 1971, now Pat. No. 3,800,043 which was a Continuation-in-part of U.S. Ser. No. 89,005, filed Nov. 12, 1970, now abandoned.

SUMMARY OF THE INVENTION

This invention describes new 1-substituted phenyl biguanide compounds and processes for their preparation. This invention further provides valuable pharmaceutical preparations which contain 1-substituted phenyl biguanide compounds as active gastric antisecretory and spasmolytic agents. A method for the treatment of gastrointestinal disorders and diseases is also described. The compounds of this invention also possess an effective degree of antihypertensive and CNS depressant activity.

BACKGROUND OF THE INVENTION

The pharmaceutical compositions which have been used as gastric antisecretory and spasmolytic agents have been such as atropine, homatropine, propantheline bromide, dicyclomine hydrochloride and other compounds which are structurally dissimilar to the biguanides of this invention. Due to the anticholinergic properties of these compounds they are known to produce undesirable side effects such as mydriasis, xerostomia, cyclopegia and other unwanted effects.

There have been a number of 1-aryl biguanides described in the literature. They have been proposed for use as antidiabetics, anorexigenic or antimalarial agents. J. H. Burn and J. R. Vane, however, in the *Brit. J. Pharmacol.* (1948), 3:346–9 tested 1-(p-chlorophenyl)biguanide for its ability to reduce gastric secretion. Their findings determined that little or no reduction of gastric secretion was associated with this compound. Contrary to this belief:

We have unexpectedly found that when an alkyl group is present in a halophenyl biguanide compound valuable pharmacologic properties exist and these compounds then unexpectedly possess useful gastric antisecretory and spasmolytic properties.

We have also found that the compounds of this invention are substantially free of the anticholinergic side-effects which accompany gastric antisecretory and spasmolytic agents.

We have further found that the compounds of this invention have a low order of toxicity.

We have still further found a simple and effective method for treating gastrointenstinal disorders and diseases, such as duodenal and peptic ulcers.

We have found that the 1-substituted phenyl biguanides of this invention also have an effective degree of antihypertensive and CNS depressant activity.

DESCRIPTION AND PREFERRED EMBODIMENT

This invention describes a class of novel chemical compounds which comprise a phenyl ring which is substituted with at least one alkyl and one halo group. This substituted phenyl radical is further attached to a biguanide chain at the 1-position. This invention also describes the non-toxic pharmaceutically acceptable salts and the method of preparing these 1-substituted biguanide compounds.

The compounds of this invention are described by the structural formula I

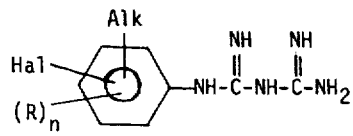

where:
n is 1–3;
Alk, Hal and R may be at any position on the ring;
Alk is loweralkyl or loweralkenyl having 1–7 carbon atoms which may be straight chained or branched;
Hal is fluoro,
  chloro,
  bromo or
  iodo; and
R is hydrogen,
  fluoro,
  chloro,
  bromo,
  iodo or
  loweralkyl having 1–7 carbon atoms which may be straight chained or branched;
with the provision that
  Alk is other than 2-methyl when Hal is chloro or 4-bromo at the same time R is hydrogen or when Hal and R are 3,5-dichloro; and
  Alk is other than 4-methyl or 4-butyl when Hal is 3-chloro and R is hydrogen;
and their non-toxic acid addition salts.

The more preferred compounds of this invention are described by structural formula I
where:
n is 1–2 and Alk is loweralkyl having 1–5 carbon atoms.

The most preferred compounds of this invention are described by structural formula I
where:
n is 1;
Alk is methyl,
  ethyl,
  propyl,
  i-propyl,
  butyl,
  i-butyl,
  sec-butyl or
  t-butyl;
Hal is fluoro,
  chloro or
  bromo; and
R is hydrogen,
  fluoro,
  chloro or
  bromo;
and their non-toxic acid addition salts.

This invention further describes a new method of treating gastrointestinal disorders and diseases which comprises the administration of the 1-substituted biguanide compounds of structural formula I
where:
n is 1–3;
Alk is loweralkyl or loweralkenyl having 1–7 carbon atoms which may be straight chained or branched;

Hal is fluoro,
chloro,
bromo or
iodo; and
R is hydrogen,
fluoro,
chloro,
bromo,
iodo or
loweralkyl having 1–7 carbon atoms which may be straight chained or branched;
and their non-toxic acid addition salts.

This invention still further describes a new method in the treatment of hypertensive disorders by the administration of a therapeutically effective amount of the 1-substituted biguanide compounds of structural formula I.

It is well known in the pharmacological arts that non-toxic acid addition salts of pharmacologically active amine compounds do not differ in activities from their free base. The salts merely provide a convenient solubility factor.

The amines of this invention may be readily converted to their non-toxic acid addition salts by customary methods in the art. The non-toxic salts of this invention are those salts the acid component of which is pharmacologically acceptable in the intended dosages; such salts would include those prepared from inorganic acids, organic acids, higher fatty acids, high molecular weight acids, etc. and include such as:

hydrochloric acid,
hydrobromic acid,
sulfuric acid,
nitric acid,
phosphoric acid,
methane sulfonic acid,
benzene sulfonic acid,
acetic acid,
propionic acid,
malic acid,
succinic acid
glycolic acid
lactic acid,
salicylic acid,
benzoic acid,
nicotinic acid,
phthalic acid,
stearic acid,
oleic acid,
abietic acid, etc.

Representative compounds of this invention which are particularly useful are as follows:
1-(2-methyl-3-chlorophenyl)biguanide
1-(2-methyl-4-chlorophenyl)biguanide
1-(2-methyl-5-chlorophenyl)biguanide
1-(2-methyl-6-chlorophenyl)biguanide
1-(3-methyl-2-chlorophenyl)biguanide
1-(3-methyl-4-chlorophenyl)biguanide
1-(3-methyl-5-chlorophenyl)biguanide
1-(3-methyl-6-chlorophenyl)biguanide
1-(4-methyl-2-chlorophenyl)biguanide
1-(4-methyl-3-chlorophenyl)biguanide
1-(2-methyl-3-bromophenyl)biguanide
1-(2-methyl-4-bromophenyl)biguanide
1-(2-methyl-5-bromophenyl)biguanide
1-(2-methyl-6-bromophenyl)biguanide
1-(3-methyl-2-bromophenyl)biguanide
1-(3-methyl-4-bromophenyl)biguanide
1-(3-methyl-5-bromophenyl)biguanide
1-(3-methyl-6-bromophenyl)biguanide
1-(4-methyl-2-bromophenyl)biguanide
1-(4-methyl-3-bromophenyl)biguanide
1-(2-methyl-3-fluorophenyl)biguanide
1-(2-methyl-4-fluorophenyl)biguanide
1-(2-methyl-5-fluorophenyl)biguanide
1-(2-methyl-6-fluorophenyl)biguanide
1-(3-methyl-2-fluorophenyl)biguanide
1-(3-methyl-4-fluorophenyl)biguanide
1-(3-methyl-5-fluorophenyl)biguanide
1-(3-methyl-6-fluorophenyl)biguanide
1-(4-methyl-2-fluorophenyl)biguanide
1-(4-methyl-3-fluorophenyl)biguanide
1-(2-methyl-3-iodophenyl)biguanide
1-(2-methyl-4-iodophenyl)biguanide
1-(2-methyl-5-iodophenyl)biguanide
1-(2-methyl-6-iodophenyl)biguanide
1-(3-methyl-2-iodophenyl)biguanide
1-(3-methyl-4-iodophenyl)biguanide
1-(3-methyl-5-iodophenyl)biguanide
1-(3-methyl-6-iodophenyl)biguanide
1-(4-methyl-2-iodophenyl)biguanide
1-(4-methyl-3-iodophenyl)biguanide
1-(2-methyl-3,4-dichlorophenyl)biguanide
1-(2-methyl-3,5-dichlorophenyl)biguanide
1-(2-methyl-3,6-dichlorophenyl)biguanide
1-(2-methyl-4,5-dichlorophenyl)biguanide
1-(2-methyl-4,6-dichlorophenyl)biguanide
1-(2-methyl-5,6-dichlorophenyl)biguanide
1-(2-methyl-3,4,5-trichlorophenyl)biguanide
1-(2-methyl-3,4,6-trichlorophenyl)biguanide
1-(2-methyl-3,5,6-trichlorophenyl)biguanide
1-(2-methyl-4,5,6-trichlorophenyl)biguanide
1-(2-methyl-3-chloro-4-bromophenyl)biguanide
1-(2-methyl-3-chloro-5-bromophenyl)biguanide
1-(2-methyl-3-chloro-6-bromophenyl)biguanide
1-(2-methyl-4-chloro-5-bromophenyl)biguanide
1-(2-methyl-4-chloro-6-bromophenyl)biguanide
1-(2-methyl-5-chloro-6-bromophenyl)biguanide
1-(2-methyl-3-bromo-4-chlorophenyl)biguanide
1-(2-methyl-3-bromo-5-chlorophenyl)biguanide
1-(2-methyl-3-bromo-6-chlorophenyl)biguanide
1-(2-methyl-4-bromo-5-chlorophenyl)biguanide
1-(2-methyl-4-bromo-6-chlorophenyl)biguanide
1-(2-methyl-5-bromo-6-chlorophenyl)biguanide
1-(2-methyl-4-chloro-6-fluorophenyl)biguanide
1-(2-methyl-4-bromo-6-fluorophenyl)biguanide
1-(2-methyl-4-fluoro-6-chlorophenyl)biguanide
1-(2-methyl-4-fluoro-6-bromophenyl)biguanide
1-(2-methyl-4-chloro-6-iodophenyl)biguanide
1-(2-methyl-4-bromo-6-iodophenyl)biguanide
1-(2-methyl-4-iodo-6-chlorophenyl)biguanide
1-(2-methyl-4-iodo-6-bromophenyl)biguanide
1-(3-methyl-2,4-dichlorophenyl)biguanide
1-(3-methyl-2,5-dichlorophenyl)biguanide
1-(3-methyl-2,6-dichlorophenyl)biguanide
1-(3-methyl-4,5-dichlorophenyl)biguanide
1-(3-methyl-4,6-dichlorophenyl)biguanide
1-(3-methyl-5,6-dichlorophenyl)biguanide
1-(3-methyl-2,4,5-trichlorophenyl)biquanide
1-(3-methyl-2,4,6-trichlorophenyl)biguanide
1-(3-methyl-2,5,6-trichlorophenyl)biguanide
1-(3-methyl-4,5,6-trichlorophenyl)biguanide
1-(4-methyl-2,3-dichlorophenyl)biguanide
1-(4-methyl-2,5-dichlorophenyl)biguanide
1-(4-methyl-2,6-dichlorophenyl)biguanide
1-(4-methyl-3,5-dichlorophenyl)biguanide
1-(4-methyl-2,3,5-trichlorophenyl)biguanide
1-(4-methyl-2,3,6-trichlorophenyl)biguanide
1-(4-methyl-2,3-dibromophenyl)biguanide
1-(4-methyl-2,5-dibromophenyl)biguanide
1-(4-methyl-2,6-dibromophenyl)biguanide
1-(4-methyl-3,5-dibromophenyl)biguanide 1-(4-methyl-2,3,5-tribromophenyl)biguanide
1-(4-methyl-2,3,6-tribromophenyl)biguanide
1-(4-methyl-2-bromo-3-chlorophenyl)biguanide
1-(4-methyl-2-bromo-5-chlorophenyl)biguanide
1-(4-methyl-2-bromo-6-chlorophenyl)biguanide
1-(4-methyl-3-bromo-5-chlorophenyl)biguanide
1-(4-methyl-2-chloro-3-bromophenyl)biguanide
1-(4-methyl-2-chloro-5-bromophenyl)biquanide
1-(4-methyl-2-chloro-3,5-dibromophenyl)biguanide
1-(4-methyl-2-chloro-3,6-dibromophenyl)biguanide
1-(4-methyl-3-chloro-2,5-dibromophenyl)biguanide
1-(4-methyl-3-chloro-2,6-dibromophenyl)biguanide
1-(4-methyl-3-chloro-5,6-dibromophenyl)biguanide
1-(4-methyl-2-chloro-5,6-dibromophenyl)biguanide
1-(4-methyl-2-bromo-3,5-dichlorophenyl)biguanide
1-(4-methyl-2-bromo-3,6-dichlorophenyl)biguanide
1-(4-methyl-3-bromo-2,5-dichlorophenyl)biguanide
1-(4-methyl-3-bromo-2,6-dichlorophenyl)biguanide
1-(4-methyl-3-bromo-5,6-dichlorophenyl)biguanide
1-(4-methyl-2-bromo-5,6-dichlorophenyl)biguanide
1-(4-methyl-2,3,5,6-tetrafluorophenyl)biguanide
1-(2-ethyl-4-chlorophenyl)biguanide
1-(2-propyl-4-chlorophenyl)biguanide
1-(2-i-propyl-4-chlorophenyl)biguanide
1-(2-butyl-4-chlorophenyl)biguanide
1-(2-i-butyl-4-chlorophenyl)biguanide
1-(2-sec-butyl-4-chlorophenyl)biguanide
1-(2-t-butyl-4-chlorophenyl)biguanide
1-(4-ethyl-2-chlorophenyl)biguanide
1-(4-propyl-2-chlorophenyl)biguanide
1-(4-i-propyl-2-chlorophenyl)biguanide
1-(4-butyl-2-chlorophenyl)biguanide
1-(4-i-butyl-2-chlorophenyl)biguanide
1-(4-sec-butyl-2-chlorophenyl)biguanide
1-(4-t-butyl-2-chlorophenyl)biguanide
1-(4-ethyl-2-bromophenyl)biguanide
1-(4-propyl-2-bromophenyl)biguanide
1-(4-i-propyl-2-bromophenyl)biguanide
1-(4-butyl-2-bromophenyl)biguanide
1-(4-i-butyl-2-bromophenyl)biguanide
1-(4-sec-butyl-2-bromophenyl)biguanide
1-(4-t-butyl-2-bromophenyl)biguanide
1-(2,4-dimethyl-6-chlorophenyl)biguanide
1-(2,4-dimethyl-6-bromophenyl)biguanide
1-(2,4-dimethyl-6-fluorophenyl)biguanide
1-(2,4-dimethyl-6-iodophenyl)biguanide
1-(2,6-dimethyl-4-chlorophenyl)biguanide
1-(2,6-dimethyl-4-bromophenyl)biguanide
1-(2,6-dimethyl-4-fluorophenyl)biguanide
1-(2,6-dimethyl-4-iodophenyl)biguanide
1-(3,5-dimethyl-2-chlorophenyl)biguanide
1-(3,5-dimethyl-4-chlorophenyl)biguanide
1-(3,5-dimethyl-2,4-dichlorophenyl)biguanide
1-(3,5-dimethyl-2,6-dichlorophenyl)biguanide
1-(3,5-dimethyl-2,4,6-trichlorophenyl)biguanide
1-(4-vinyl-2-chlorophenyl)biguanide
1-(4-allyl-2-chlorophenyl)biguanide
1-(4-methallyl-2-chlorophenyl)biguanide
1-([4-(4-pentenyl)-2-chlorophenyl]biguanide
1-(4-propargyl-2-chlorophenyl)biguanide The compounds of this invention may be prepared by the following general procedures.

Condensation of cyanoguanide and a substituted aniline in the presence of an equimolar amount of a mineral acid results in the corresponding substituted phenylbiguanide.

The following reaction illustrates this synthesis:

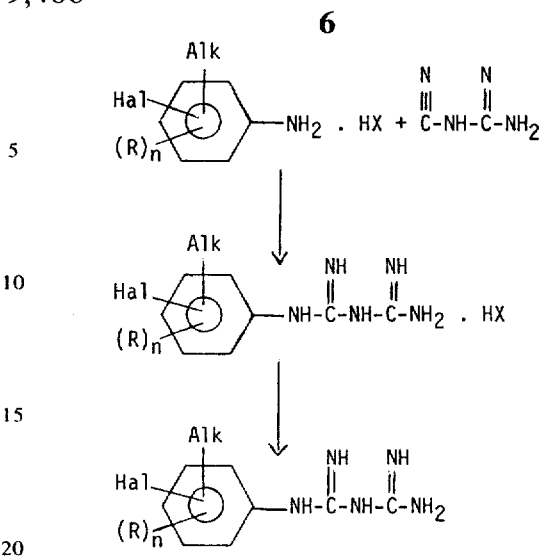

where:
HX is a mineral acid.

The reaction is preferably carried out on the aniline salt either in a polar medium or neat and using increased temperatures. The salt used may be any acid addition amine salt but preferably the salt of a mineral acid. The polar medium may be aqueous, partially aqueous or a non-aqueous solution. It is convenient to choose a solvent that will reflux at the desired reaction temperature. The more preferred solvents are water or alcohol but other solvents may be used such as DMSO, diethyleneglycol, ethyleneglycol, tetrahydrofuran, dimethylformamide, etc. The reaction should also be carried out at a temperature which is high enough so that condensation takes place readily, but not sufficient to decompose the biguanide formed. The reaction temperature can vary from room temperature to about 250°C although it is preferable to run the reaction at temperatures from about 50°C to 150°C. The biguanide salt which is formed can be converted to the free base with a metal hydroxide or alkoxide solution. The isolation of the desired biguanide can be carried out by any method known in the art.

A special embodiment of this invention describes a novel process for preparing the instant biguanide compounds. We have unexpectedly found that when the reaction of the substituted aniline with cyanoguanidine takes place in a mildly acidic solvent which is non-nucleophilic then the condensation takes place in high yield. We have further found that this reaction works on highly hindered as well as highly unreactive anilines. It is preferable to use a phenolic solvent such as a phenol, cresol, xylol, etc. The reaction can be carried out at temperatures from room temperature to about 150°C; however, it is preferable to use temperatures between 60° and 100°C. Isolation of the reaction product can be carried out by chemical or physical techniques; however, it is convenient to precipitate the salt of the product out of the reaction mixture with a non-polar solvent such as ether or by making the reaction mixture alkaline and extracting with ether.

The starting anilines are either known or may be prepared by known alkylation and halogenation techniques. Thus, alkylation may be carried out on an acetanilide using an alkyl halide and aluminum chloride under Friedel-Crafts conditions to obtain desired substitution in the ortho and para positions. Chlorination or bromination of an acetanilide or aniline may be carried out in acetic acid, or in the presence of a small amount of iodine dissolved in an inert solvent such as carbon tetrachloride. A solution of chlorine or bromine is then added while the temperature is held near 0°C. This halogenates in the ortho and/or para positions. Alkylation or halogenation followed by halogenation or alkylation results in the desired alkyl-halo anilide. Further alkylation or halogenation results in the desired polysubstituted anilides. Deacylation with 50% sulfuric acid or alcoholic potassium hydroxide results in the aniline.

Iodination can also be carried out by methods known in the art using iodine monochloride (CII).

An acetanilide may be alkylated and/or halogenated as above to obtain the ortho and/or para halo and/or alkyl acetanilide. A Friedel-Crafts reaction of the latter with acetyl chloride results in the introduction of the acetyl group into the para position to the acetanilide. The acetamido group may then be deacylated followed by deamination through a diazonium to obtain desired meta alkyl and/or halo substitution. The acetophenone may then be converted to the oxime and by Beckmann Rearrangement can result in the acetamide. Deacylation results in the aniline. Further alkylation and/or halogenation results in ortho/para substitution.

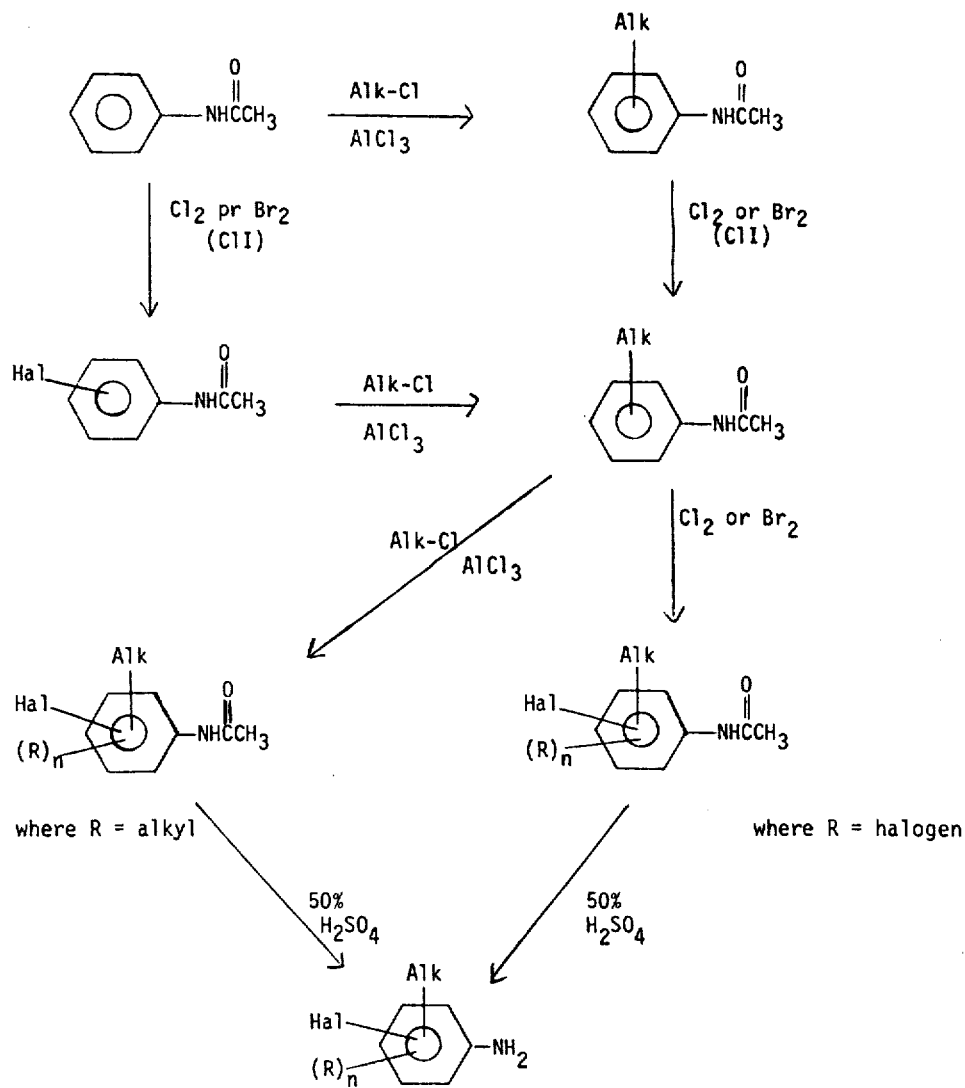

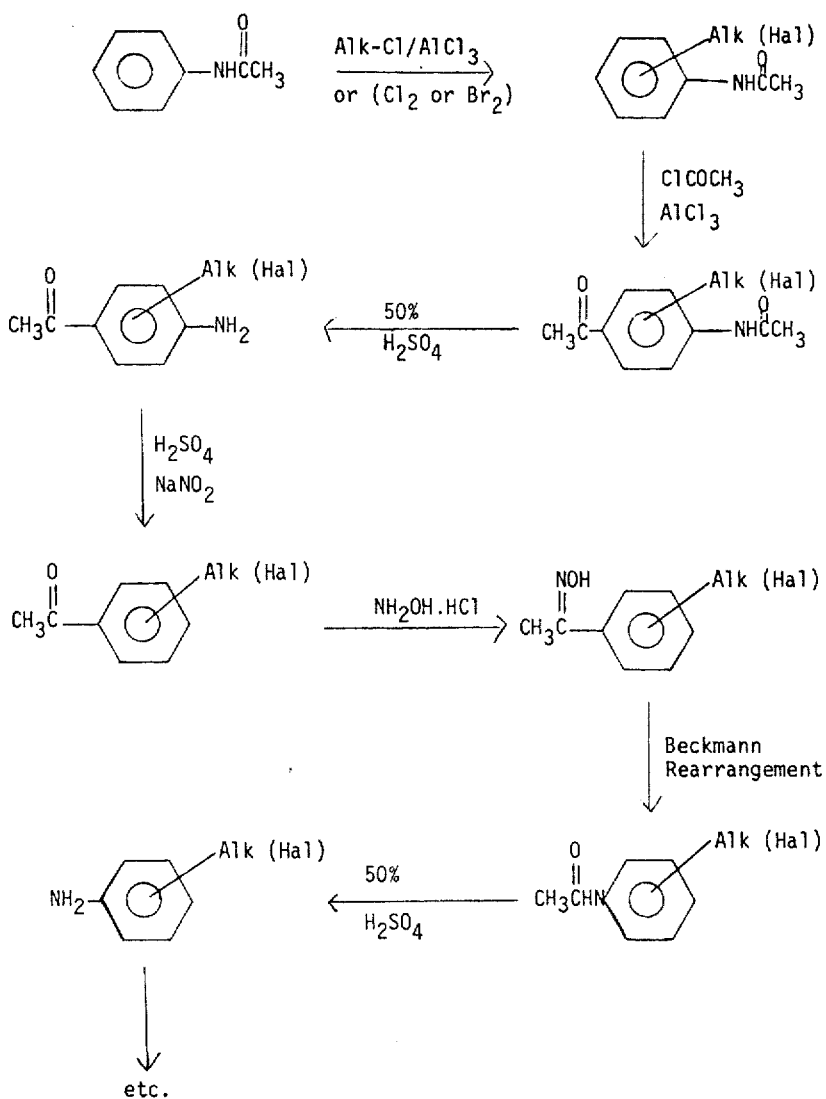
Nitration of the above anilides followed by reduction to the amine which is then diazotized to the diazonium fluoroborate and thermally decomposed results in the fluoroanilide. Diazotization followed by a Sandmeyer type reaction with cuprous chloride, cuprous bromide or cuprous iodide results in the haloanilide.
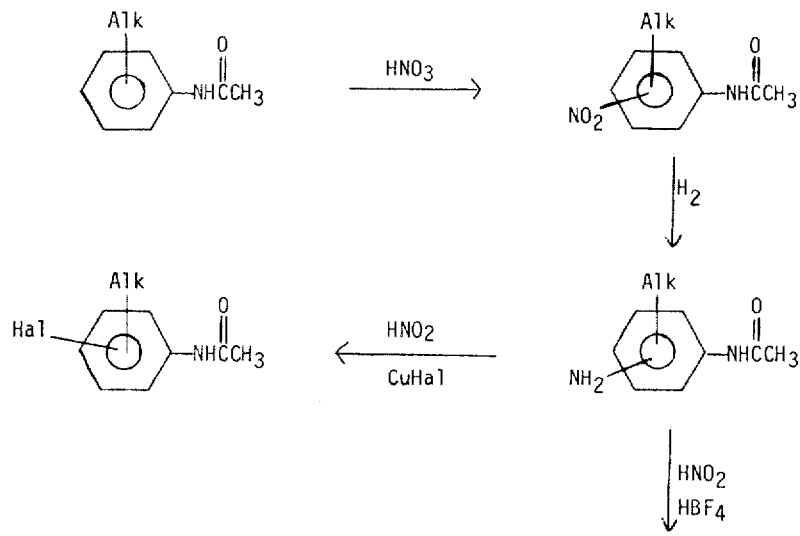

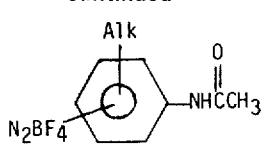

↓ Δ

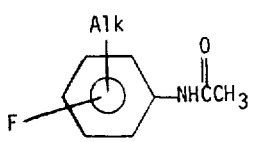

Reactions can also be carried out on 1-substituted phenylbiguanide compounds which result in further substituted products. In this regard, we have found that 1-halo and/or alkyl phenylbiguanides may be halogenated to obtain halo alkyl substituted products. These in turn can be reacted as above to the desired compound.

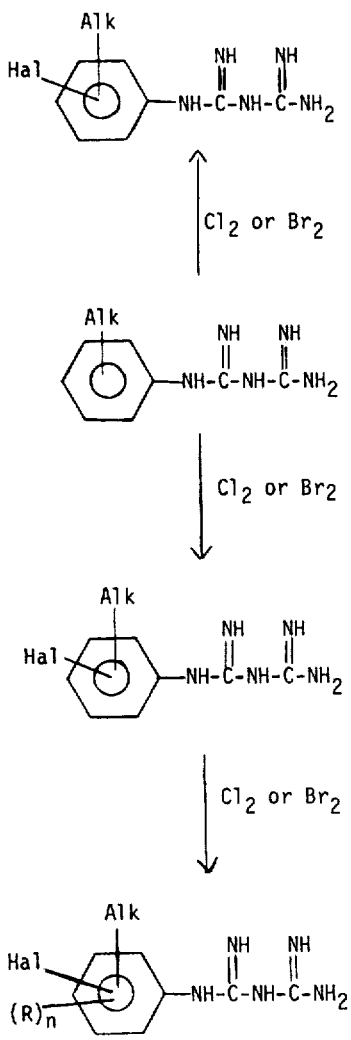

The compounds of this invention have a useful degree of gastric anti-secretory activity and are effective in reducing the volume and the acidity of the gastric fluid in humans and mammals. Further, these compounds produce a considerable spasmolytic action on the gastrointestinal musculature, i.e., they reduce the peristaltic action of the gastrointestinal musculature which is manifested by a delay in gastric emptying time. It should be further noted that these compounds are also characterized by their low acute oral toxicity.

In particular the 1-substituted phenylbiguanides as herein described are useful in the treatment of such gastrointestinal disorders and diseases as duodenal ulcer and peptic ulcer.

The instant compounds may be used alone or in combination with other known antacids such as aluminum hydroxide, magnesium hydroxide, magnesium trisilicate, aluminum glycinate, calcium carbonate and the like.

The compounds of this invention possess blood-pressure lowering activities and are also useful as antihypertensive agents.

For all these purposes, the biguanides of this invention can be normally administered orally or parenterally. Orally they may be administered as tablets, aqueous or oily suspension, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents, preserving agents and the like, in order to provide a pharmaceutically elegant and palatable preparation.

The dosage regimen in carrying out the methods of this invention is that which insures maximum therapeutic response until improvement is obtained and thereafter the minimum effective level which gives relief. Thus, in general, the dosages are those that are therapeutically effective in the treatment of gastrointestinal disease conditions or symptoms, such as duodenal and peptic ulcer, and in the alleviation of hypertensive disorders. In general, the daily dose can be between about 0.5 mg/kg and 70 mg/kg (preferably in the range of 2–25 mg/kg/day), bearing in mind, of course, that in selecting the appropriate dosage in any specific case, consideration must be given to the patient's weight, general health, age, and other factors which may influence response to the drug.

Various tests in animals have been carried out to show the ability of the compounds of this invention to exhibit reactions that can be correlated with activity in humans. These tests involve such factors as the effect of the 1-substituted phenylbiguanides on gastric secretion, their spasmolytic effect, their mydriatic effect and determination of their toxicity. It has been found that the compounds of this invention when tested in the above variety of situations show a marked activity.

One such test is the gastric secretion test. This test is carried out as follows. Shay rats are fasted for 4–8 hours, and water is given ad lib. The rats are selected at random and separated into groups of 10. The animals are treated intraduodenally (I.D.) with the test compound or the vehicle immediately subsequently to the ligation of the stomach at the pyloric sphincter. The animals are sacrificed with chloroform at 4 hours post-drug administration, the stomach is removed and its contents are assayed for volume, pH and total acids.

A second gastric secretion test is carried out on the dog. This is outlined in the *Handbook of Physiology*, Section 6: Alimentary Canal, Volume II: Secretion. American Physiology Society, Washington, D.C., 1967.

It has been found that the compounds of this invention when subjected to the above gastric secretion tests display marked ability to decrease gastric volume and gastric activity. These tests are known to correlate well with gastric activity in humans and are standard tests used to determine anti-secretory properties.

To determine the anti-ulcer effectiveness the following test is employed: Male Wistar rats (130–150 grams) are fasted for 24 hours, then given reserpine at 5 mg/kg i.p. Twenty-four hours later, the stomachs are removed and examined for ulceration. Ulcers are graded on a 0–4 scale and the number of ulcers is recorded. Pretreatment with the biguanide compounds produces a decrease in ulcer grade and the number of ulcers compared to the control reserpine-treated rats.

Determination of anti-spasmolytic properties can be carried out by the procedure as outlined by D. A. Brodie and S. K. Kundrats in their article entitled "Effect of Drugs on Gastric Emptying in Rats", *Fed. Proc.* 24:714 (1965).

Mydriasis is detected by the procedure of R. A. Turner, *Screening Methods in Pharmacology*, Academic Press, New York, and London, pp. 174–5, 1965. Acute toxicity is calculated according to the standard Litchfield-Wilcoxon procedure.

In view of the results of these tests, the pharmacological data clearly indicates that the 1-substituted phenylbiguanides of this invention can be considered to be active gastric anti-secretory and anti-spasmolytic agents which are substantially free of anti-cholinergic side effects and having a low toxicity.

Tests in animals have also been carried out to show the ability of compounds of this invention to inhibit reactions that can be correlated with hypertensive effects in humans. One such test is outlined by Jacques de Champlain, Lawrence R. Krahoff and Julius Axelrod in *Circulation Research* XXIII:479 (1968). This testing method is known to correlate well with hypertensive activity in humans and is a standard test used to determine anti-hypertensive properties. In view of the results of this test, the 1-substituted phenylbiguanides of this invention can be considered to be active anti-hypertensive agents.

To determine the CNS depressent effectiveness of the compounds of Formula I, the suppression depressant spontaneous motor activity is evaluated in normal mice (18–22 g) and immature rats (90–100 g) by a modification of the Dew method: Dews, *Brit. J. Pharmacol:* 8, 46 (1953). Results of this test indicate that a relative increase in depressant activity is evident.

The following are detailed examples which show the preparation of the compounds of this invention. They are to be construed as illustrations of said compounds and not as limitations thereof.

EXAMPLE 1

1-(p-Tolyl)biguanide dihydrochloride

A stirred mixture of 4.3 g. (.03 mole) of p-toluidine hydrochloride and 2.5 g. (0.03 mole) of cyanoguanidine is immersed in a a 210°C. oil bath for fifteen minutes. The resulting amber glass-like reaction product is dissolved in 100 ml of water, alkalized with 40% sodium hydroxide solution, and extracted with 250 ml of ether. The ether layer is backwashed twice with 10 ml of water, dried over sodium carbonate, filtered, and the ether solution made strongly acidic with a saturated etheral hydrochloric acid solution. The precipitate is collected on a filter, washed twice with 50 ml of anhydrous ether, and dried in vacuo at 25°C to obtain 1-(p-tolyl)biguanide dihydrochloride.

When the procedures of Example 1 is followed and an equimolar amount of the following starting materials are used in place of p-toluidine then the corresponding product is obtained.

| STARTING MATERIAL | PRODUCT |
| --- | --- |
| o-toluidine | 1-(o-tolyl)biguanide |
| m-toluidine | 1-(m-tolyl)biguanide |
| 2,3-xylidine | 1-(2,3-xylyl)biguanide |
| 2,4-xylidine | 1-(2,4-xylyl)biguanide |
| 2,5-xylidine | 1-(2,5-xylyl)biguanide |
| 2,6-xylidine | 1-(2,6-xylyl)biguanide |
| 3,4-xylidine | 1-(3,4-xylyl)biguanide |
| 3,5-xylidine | 1-(3,5-xylyl)biguanide |
| o-ethylaniline | 1-(o-ethylphenyl)biguanide |
| m-ethylaniline | 1-(m-ethylphenyl)biguanide |
| p-ethylaniline | 1-(p-ethylphenyl)biguanide |
| o-propylaniline | 1-(o-propylphenyl)biguanide |
| o-i-propylaniline | 1-(o-i-propylphenyl)biguanide |
| o-butylaniline | 1-(o-butylphenyl)biguanide |
| o-i-butylaniline | 1-(o-i-butylphenyl)biguanide |
| o-sec-butylaniline | 1-(o-sec-butylphenyl)biguanide |
| o-t-butylaniline | 1-(o-t-butylphenyl)biguanide |
| o-pentylaniline | 1-(o-pentylphenyl)biguanide |
| o-hexylaniline | 1-(o-hexylphenyl)biguanide |
| o-heptylaniline | 1-(o-heptylphenyl)biguanide |
| m-propylaniline | 1-(m-propylphenyl)biguanide |
| m-i-propylaniline | 1-(m-i-propylphenyl)biguanide |
| m-butylaniline | 1-(m-butylphenyl)biguanide |
| m-i-butylaniline | 1-(m-i-butylphenyl)biguanide |
| m-t-butylaniline | 1-(m-t-butylphenyl)biguanide |
| p-propylaniline | 1-(propylphenyl)biguanide |
| p-i-propylaniline | 1-(propylphenyl)biguanide |
| p-butylaniline | 1-(p-butylphenyl)biguanide |
| p-i-butylaniline | 1-(p-i-butylphenyl)biguanide |

| STARTING MATERIAL | PRODUCT |
|---|---|
| p-sec-butylaniline | 1-(p-sec-butylphenyl)biguanide |
| p-t-butylaniline | 1-(p-t-butylphenyl)biguanide |
| p-pentylaniline | 1-(p-pentylphenyl)biguanide |
| p-hexylaniline | 1-(p-hexylphenyl)biguanide |
| p-heptylaniline | 1-(p-heptylphenyl)biguanide |
| 2,4-diethylaniline | 1-(2,4-diethylphenyl)biguanide |
| 2-methyl-4-ethylaniline | 1-(2-methyl-4-ethylphenyl)biguanide |
| 2-ethyl-4-methylaniline | 1-(2-ethyl-4-methylphenyl)biguanide |

EXAMPLE 2

1-(2-Chloro-4-methylphenyl)biguanide hydrochloride

To 0.05 moles of 1-(p-tolyl)biguanide dissolved in 75 ml of acetic acid is added 9 ml of concentrated hydrochloric acid followed by 1.74 g. (0.0164 moles) of sodium chlorate in 4 ml of water. The temperature is held below 25°C with stirring for 10 hours and then cooled in an ice bath. To the reaction mixture is added 40% sodium hydroxide solution and extracted with ether. The ether is worked with water, dried over magnesium sulfite and evaporated to dryness. The hydrochloride salt is then prepared with ethanolic hydrochloric acid to obtain 1-(2-chloro-4-methylphenyl)biguanide hydrochloride.

When the biguanides of Example 1 are used in the above reaction then the products prepared are shown below.

1-(2-methyl-6-chlorophenyl)biguanide
1-(2-chloro-3-methylphenyl)biguanide
1-(2,3-dimethyl-4-chlorophenyl)biguanide
1-(2,4-dimethyl-6-chlorophenyl)biguanide
1-(2,5-dimethyl-4-chlorophenyl)biguanide
1-(2,6-dimethyl-4-chlorophenyl)biguanide
1-(2-chloro-3,4-dimethylphenyl)biguanide
1-(3,5-dimethyl-4-chlorophenyl)biguanide
1-(2-ethyl-6-chlorophenyl)biguanide
1-(2-chloro-3-ethylphenyl)biguanide
1-(2-chloro-4-ethylphenyl)biguanide
1-(2-propyl-6-chlorophenyl)biguanide
1-(2-i-propyl-6-chlorophenyl)biguanide
1-(2-butyl-6-chlorophenyl)biguanide
1-(2-i-butyl-6-chlorophenyl)biguanide
1-(2-sec-butyl-6-chlorophenyl)biguanide
1-(2-t-butyl-6-chlorophenyl)biguanide
1-(2-pentyl-6-chlorophenyl)biguanide
1-(2-hexyl-6-chlorophenyl)biguanide
1-(2-heptyl-6-chlorophenyl)biguanide
1-(2-chloro-3-propylphenyl)biguanide
1-(2-chloro-3-i-propylphenyl)biguanide
1-(2-chloro-3-i-propylphenyl)biguanide
1-(2-chloro-3-i-butylphenyl)biguanide
1-(2-chloro-3-t-butylphenyl)biguanide
1-(2-chloro-4-propylphenyl)biguanide
1-(2-chloro-4-i-propylphenyl)biguanide
1-(2-chloro-4-butylphenyl)biguanide
1-(2-chloro-4-i-butylphenyl)biguanide
1-(2-chloro-4-sec-butylphenyl)biguanide
1-(2-chloro-4-t-butylphenyl)biguanide
1-(2-chloro-4-pentylphenyl)biguanide
1-(2-chloro-4-hexylphenyl)biguanide
1-(2-chloro-4-heptylphenyl)biguanide
1-(2,4-diethyl-6-chlorophenyl)biguanide
1-(2-methyl-4-ethyl-6-chlorophenyl)biguanide
1-(2-ethyl-4-methyl-6-chlorophenyl)biguanide

EXAMPLE 3

1-(2-Chloro-6-ethylphenyl)biguanide hydrochloride

A mixture of 3 g. (0.0156 mole) of 2-chloro-6-ethylaniline hydrochloride and 1.35 g. (0.016 mole) of cyanoguanidine in 25 ml of m-cresol is heated on a steam bath for 1 hour. The reaction mixture is then cooled and 250 ml of ether is added. The preciptate is filtered off and dissolved in 100 ml of warm water, charcoaled and filtered and cooled in an ice bath. 10% sodium hydroxide solution is then added to make the mixture strongly basic. The mixture is then filtered and washed with water. This is then dissolved in methanol, the pH is adjusted to 7 with methanolic hydrochloric acid and the mixture evaporated to dryness, triturated with ether and filtered to obtain 1-(2-chloro-6-ethylphenyl)biguanide hydrochloride (m.p. 209°–210°C).

When an equimolar amount of the starting materials shown below are used in place of 2-chloro-6-ethylaniline in the above procedure, then the corresponding product is obtained.

| STARTING MATERIAL | PRODUCT |
|---|---|
| 2-methyl-3-chloroaniline | 1-(2-methyl-3-chlorophenyl)biguanide |
| 2-methyl-4-chloroaniline | 1-(2-methyl-4-chlorophenyl)biguanide |
| 2-methyl-5-chloroaniline | 1-(2-methyl-5-chlorophenyl)biguanide |
| 2-methyl-6-chloroaniline | 1-(2-methyl-6-chlorophenyl)biguanide |
| 3-methyl-2-chloroaniline | 1-(2-methyl-2-chlorophenyl)biguanide |
| 3-methyl-4-chloroaniline | 1-(3-methyl-4-chlorophenyl)biguanide |
| 3-methyl-5-chloroaniline | 1-(3-methyl-5-chlorophenyl)biguanide |
| 3-methyl-6-chloroaniline | 1-(3-methyl-6-chlorophenyl)biguanide |
| 4-methyl-2-chloroaniline | 1-(4-methyl-2-chlorophenyl)biguanide |
| 4-methyl-3-chloroaniline | 1-(4-methyl-3-chlorophenyl)biguanide |
| 2-methyl-3-bromoaniline | 1-(2-methyl-3-bromophenyl)biguanide |
| 2-methyl-4-bromoaniline | 1-(2-methyl-4-bromophenyl)biquanide |
| 2-methyl-5-bromoaniline | 1-(2-methyl-5-bromophenyl)biguanide |
| 2-methyl-6-bromoaniline | 1-(2-methyl-6-bromophenyl)biguanide |
| 3-methyl-2-bromoaniline | 1-(3-methyl-2-bromophenyl)biguanide |
| 3-methyl-4-bromoaniline | 1-(3-methyl-4-bromophenyl)biguanide |
| 3-methyl-5-bromoaniline | 1-(3-methyl-5-bromophenyl)biguanide |
| 3-methyl-6-bromoaniline | 1-(3-methyl-6-bromophenyl)biguanide |
| 4-methyl-2-bromoaniline | 1-(4-methyl-2-bromophenyl)biguanide |
| 4-methyl-3-bromoaniline | 1-(4-methyl-3-bromophenyl)biguanide |
| 2-methyl-3-fluoroaniline | 1-(2-methyl-3-fluorophenyl)biguanide |

-continued

| STARTING MATERIAL | PRODUCT |
| --- | --- |
| 2-methyl-3-fluoroaniline | 1-(2-methyl-4-fluorophenyl)biguanide |
| 2-methyl-4-fluoroaniline | 1-(2-methyl-4-fluorophenyl)biguanide |
| 2-methyl-5-fluoroaniline | 1-(2-methyl-5-fluorophenyl)biguanide |
| 2-methyl-6-fluoroaniline | 1-(2-methyl-6-fluorophenyl)biguanide |
| 3-methyl-2-fluoroaniline | 1-(3-methyl-2-fluorophenyl)biguanide |
| 3-methyl-4-fluoroaniline | 1-(3-methyl-4-fluorophenyl)biguanide |
| 3-methyl-5-fluoroaniline | 1-(3-methyl-5-fluorophenyl)biguanide |
| 3-methyl-6-fluoroaniline | 1-(3-methyl-6-fluorophenyl)biguanide |
| 2-ethyl-4-chloroaniline | 1-(2-ethyl-4-chlorophenyl)biguanide |
| 2-propyl-4-chloroaniline | 1-(2-propyl-4-chlorophenyl)biguanide |
| 2-i-propyl-4-chloroaniline | 1-(2-i-propyl-4-chlorophenyl)biguanide |
| 2-butyl-4-chloroaniline | 1-(2-butyl-4-chlorophenyl)biguanide |
| 2-i-butyl-4-chloroaniline | 1-(2-i-butyl-4-chlorophenyl)biguanide |
| 2-sec-butyl-4-chloroaniline | 1-(2-sec-butyl-4-chlorophenyl)biguanide |
| 2-t-butyl-4-chloroaniline | 1-(2-t-butyl-4-chlorophenyl)biguanide |
| 4-ethyl-2-chloroaniline | 1-(4-ethyl-2-chlorophenyl)biguanide |
| 4-propyl-2-chloroaniline | 1-(4-propyl-2-chlorophenyl)biguanide |
| 4-i-propyl-2-chloroaniline | 1-(4-i-propyl-2-chlorophenyl)biguanide |
| 4-butyl-2-chloroaniline | 1-(4-butyl-2-chlorophenyl)biguanide |
| 4-i-butyl-2-chloroaniline | 1-(4-i-butyl-2-chlorophenyl)biguanide |
| 4-sec-butyl-2-chloroaniline | 1-(4-sec-butyl-2-chlorophenyl)biguanide |
| 4-t-butyl-2-chloroaniline | 1-(4-t-butyl-2-chlorophenyl)biguanide |
| 4-ethyl-2-bromoaniline | 1-(4-ethyl-2-bromophenyl)biguanide |
| 4-propyl-2-bromoaniline | 1-(4-propyl-2-bromophenyl)biguanide |
| 4-i-propyl-2-bromoaniline | 1-(4-i-propyl-2-bromophenyl)biguanide |
| 4-butyl-2-bromoaniline | 1-(4-butyl-2-bromophenyl)biguanide |
| 4-i-butyl-2-bromoaniline | 1-(4-i-butyl-2-bromophenyl)biguanide |
| 4-sec-butyl-2-bromoaniline | 1-(4-sec-butyl-2-bromophenyl)biguanide |
| 4-t-butyl-2-bromoaniline | 1-(4-t-butyl-2-bromophenyl)biguanide |
| 4-methyl-2-fluoroaniline | 1-(4-methyl-2-fluorophenyl)biguanide |
| 4-methyl-3-fluoroaniline | 1-(4-methyl-3-fluorophenyl)biguanide |
| 2-methyl-3-iodoaniline | 1-(2-methyl-3-iodophenyl)biguanide |
| 2-methyl-4-iodoaniline | 1-(2-methyl-4-iodophenyl)biguanide |
| 2-methyl-5-iodoaniline | 1-(2-methyl-5-iodophenyl)biguanide |
| 2-methyl-6-iodoaniline | 1-(2-methyl-6-iodophenyl)biguanide |
| 3-methyl-2-iodoaniline | 1-(3-methyl-2-iodophenyl)biguanide |
| 3-methyl-4-iodoaniline | 1-(3-methyl-4-iodophenyl)biguanide |
| 3-methyl-5-iodoaniline | 1-(3-methyl-5-iodophenyl)biguanide |
| 3-methyl-6-iodoaniline | 1-(3-methyl-6-iodophenyl)biguanide |
| 4-methyl-2-iodoaniline | 1-(4-methyl-2-iodophenyl)biguanide |
| 4-methyl-3-iodoaniline | 1-(4-methyl-3-iodophenyl)biguanide |

EXAMPLE 4

1-(2,6-Dichloro-4-methylphenyl)biguanide hydrochloride

To 0.2 moles of 1-(2-chloro-4-methylphenyl)biguanide dissolved in 250 ml of acetic acid is added 35 ml of concentrated hydrochloric acid followed dropwise by 6.95 g (0.0653 mole) of sodium chlorate in 15 ml of water. The temperature is held below 25°C with stirring for 15 hours. To this is added 40% sodium hydroxide solution, ice and ether and extracted. The ether layer is washed with water, dried over magnesium sulfate and evaporated to dryness. The residue is added to 75 ml of MeOH and 75 ml water and stirred in an ice bath and filtered. The residue is added to ethanolic hydrochloric acid and results in 1-(2,6-dichloro-4-methylphenyl)-biguanide hydrochloride.

When the procedure of Example 4 is followed but an equimolar amount of the starting materials below are used in place of 1-(2-chloro-4-methylphenyl)biguanide, then the corresponding product is obtained.

| STARTING MATERIAL | PRODUCT |
| --- | --- |
| 1-(2-methyl-4-chlorophenyl)biguanide | 1-(2-methyl-4,6-dichlorophenyl)biguanide |
| 1-(2-methyl-3,4-dichlorophenyl)biguanide | 1-(2-methyl-3,4,6-trichlorophenyl)biguanide |
| 1-(2-methyl-5-bromophenyl)biguanide | 1-(2-methyl-4-chloro-5-bromophenyl)biguanide |
| 1-(2-methyl-6-bromophenyl)biguanide | 1-(2-methyl-4-chloro-6-bromophenyl)biguanide |
| 1-(2-methyl-4-bromophenyl)biguanide | 1-(2-methyl-4-bromo-6-chlorophenyl)biguanide |
| 1-(2-methyl-6-fluorophenyl)biguanide | 1-(2-methyl-4-chloro-6-fluorophenyl)biguanide |
| 1-(2-methyl-4-fluorophenyl)biguanide | 1-(2-methyl-4-fluoro-6-chlorophenyl)biguanide |
| 1-(3-methyl-4-chlorophenyl)biguanide | 1-(3-methyl-2,4-dichlorophenyl)biguanide |
| 1-(3-methyl-5-chlorophenyl)biguanide | 1-(3-methyl-2,5-dichlorophenyl)biguanide |
| 1-(3-methyl-2-chlorophenyl)biguanide | 1-(3-methyl-2,6-dichlorophenyl)biguanide |
| 1-(3-methyl-4-chlorophenyl)biguanide | 1-(3-methyl-4,6-dichlorophenyl)biguanide |
| 1-(3-methyl-4,5-dichlorophenyl)biguanide | 1-(3-methyl-2,4,5-trichlorophenyl)biguanide |
| 1-(3-methyl-2,4-dichlorophenyl)biguanide | 1-(3-methyl-2,4,6-trichlorophenyl)biguanide |
| 1-(4-methyl-3-chlorophenyl)biguanide | 1-(4-methyl-2,5-dichlorophenyl)biguanide |
| 1-(4-methyl-2-chlorophenyl)biguanide | 1-(4-methyl-2,6-dichlorophenyl)biguanide |
| 1-(4-methyl-2,3-dichlorophenyl)biguanide | 1-(4-methyl-2,3,6-trichlorophenyl)biguanide |
| 1-(4-methyl-2-bromophenyl)biguanide | 1-(4-methyl-2-bromo-6-chlorophenyl)biguanide |

-continued

| STARTING MATERIAL | PRODUCT |
|---|---|
| 1-(4-methyl-3-bromophenyl)biguanide | 1-(4-methyl-2-chloro-5-bromophenyl)biguanide |
| 1-(4-methyl-2-bromo-3-chlorophenyl)biguanide | 1-(4-methyl-2-bromo-3,6-dichlorophenyl)biguanide |
| 1-(4-methyl-2-chloro-3-bromophenyl)biguanide | 1-(4-methyl-3-bromo-2,6-dichlorophenyl)biguanide |
| 1-(2-methyl-3-chlorophenyl)biguanide | 1-(2-methyl-3,6-dichlorophenyl)biguanide |
| 1-(2-methyl-3-bromophenyl)biguanide | 1-(2-methyl-3-bromo-6-chlorophenyl)biguanide |
| 1-(2,4-dimethylphenyl)biguanide | 1-(2,4-dimethyl-6-chlorophenyl)biguanide |
| 1-(2,6-dimethylphenyl)biguanide | 1-(2,6-dimethyl-4-chlorophenyl)biguanide |
| 1-(3,5-dimethylphenyl)biguanide | 1-(3,5-dimethyl-2-chlorophenyl)biguanide |
| 1-(3,5-dimethylphenyl)biguanide | 1-(3,5-dimethyl-4-chlorophenyl)biguanide |
| 1-(3,5-dimethyl-4-chlorophenyl)biguanide | 1-(3,5-dimethyl-2,4-dichlorophenyl)biguanide |
| 1-(3,5-dimethyl-2-chlorophenyl)biguanide | 1-(3,5-dimethyl-2,6-dichlorophenyl)biguanide |
| 1-(3,5-dimethyl-4-chlorophenyl)biguanide | 1-(3,5-dimethyl-2,4,6-trichlorophenyl)biguanide |

EXAMPLE 5

1-(2-Bromo-4-methylphenyl)biguanide

To a slurry of 10 g. (0.0523 mole) of 1-(p-tolyl)-biguanide in 175 ml of water is added dropwise 8.4 g. (0.053 mole) of bromine over a period of 3 hours. The reaction mixture is cooled and the unreacted bromine discharged with sodium bisulfite. The mixture is made strongly alkaline and extracted into ether. The ether layer is dried over $Na_2SO_4$, charcoaled, filtered and evaporated to obtain 1-(2-bromo-4-methylphenyl)-biguanide.

When two moles of bromine is used in the above example, then the product obtained is 1-(2,6-dibromo-4-methylphenyl)biguanide.

When the above procedure is followed using the starting materials below, then the corresponding product is obtained.

| STARTING MATERIAL | PRODUCT |
|---|---|
| 1-(2-methyl-3-chlorophenyl)biguanide | 1-(2-methyl-3-chloro-6-bromophenyl)biguanide |
| 1-(2-methyl-6-chlorophenyl)biguanide | 1-(2-methyl-4-bromo-6-chlorophenyl)biguanide |
| 1-(2-methyl-6-fluorophenyl)biguanide | 1-(2-methyl-4-bromo-6-fluorophenyl)biguanide |
| 1-(2-methyl-4-fluorophenyl)biguanide | 1-(2-methyl-4-fluoro-6-bromophenyl)biguanide |
| 1-(2-methyl-6-iodophenyl)biguanide | 1-(2-methyl-4-bromo-6-iodophenyl)biguanide |
| 1-(2-methyl-4-iodophenyl)biguanide | 1-(2-methyl-4-iodo-6-bromophenyl)biguanide |
| 1-(4-methyl-5-bromophenyl)biguanide | 1-(4-methyl-2,5-dibromophenyl)biguanide |
| 1-(4-methylphenyl)biguanide | 1-(4-methyl-2,6-dibromophenyl)biguanide |
| 1-(4-methyl-2,3-dibromophenyl)biguanide | 1-(4-methyl-2,3,6-tribromophenyl)biguanide |
| 1-(4-methyl-6-chlorophenyl)biguanide | 1-(4-methyl-2-bromo-6-chlorophenyl)biguanide |
| 1-(4-methyl-3-chloro-5-bromophenyl)biguanide | 1-(4-methyl-3-chloro-2,5-dibromophenyl)biguanide |
| 1-(4-methyl-2-bromo-3-chlorophenyl)biguanide | 1-(4-methyl-3-chloro-2,6-dibromophenyl)biguanide |
| 1-(2,4-dimethylphenyl)biguanide | 1-(2,4-dimethyl-6-bromophenyl)biguanide |
| 1-(2,6-dimethylphenyl)biguanide | 1-(2,6-dimethyl-4-bromophenyl)biguanide |

EXAMPLE 6

When the procedure of Example 3 is followed using the hydrochloride salt of
4-vinyl-2-chloroaniline
4-allyl-2-chloroaniline
4-methallyl-2-chloraniline
4-(4-pentenyl-2-chloroaniline and
4-propargyl-2-chloroaniline
in place of 2-chloro-6-ethylaniline hydrochloride then the products prepared are
1-(4-vinyl-2-chlorophenyl)biguanide
1-(4-allyl-2-chlorophenyl)biguanide
1-(4-methallyl-2-chlorophenyl)biguanide
1-[4-(4-pentenyl)-2-chlorophenyl]biguanide
1-(4-propargyl-2-chlorophenyl)biguanide

We claim:

1. A method of treating gastrointestinal hyperacidity or ulceration in a human or mammal in need thereof, which comprises the oral or parenteral administration of an effective gastric anti-ulceration or anti-secretory amount of 1-(2-iodo-4-methylphenyl)biguanide.

2. A method of treating gastrointestinal hyperacidity or ulceration in a human or mammal in need thereof, which comprises the oral or parenteral administration of an effective gastric anti-ulceration or anti-secretory amount of 1-(2,6-dichloro-4-methylphenyl)biguanide.

3. A method of treating gastrointestinal hyperacidity or ulceration in a human or mammal in need thereof, which comprises the oral or parenteral administration of an effective gastric anti-ulceration or anti-secretory amount of 1-(2,6-dichloro-4-ethylphenyl)biguanide.

4. A method of treating gastrointestinal hyperacidity or ulceration in a human or mammal in need thereof, which comprises the oral or parenteral administration of an effective gastric anti-ulceration or anti-secretory amount of 1-(2-chloro-4-methyl-6-bromophenyl)-biguanide.

5. A method of treating gastrointestinal hyperacidity or ulceration in a human or mammal in need thereof, which comprises the oral or parenteral administration of an effective gastric anti-ulceration or anti-secretory amount of 1-(2-methyl-4-bromophenyl)biguanide.

6. A method of treating gastrointestinal hyperacidity or ulceration in a human or mammal in need thereof, which comprises the oral or parenteral administration of an effective gastric anti-ulceration or anti-secretory amount of 1-(2-iodo-4-ethylphenyl)biguanide.

* * * * *